United States Patent [19]

Rey et al.

[11] Patent Number: 4,714,074

[45] Date of Patent: Dec. 22, 1987

[54] METHOD FOR PROTECTING HUMAN OR ANIMAL ORGANS AGAINST RADIATION

[75] Inventors: Pierre Rey, Lagny; Clement Abbou, Fontenay s/Bois; Jacqueline Leandri, Paris; Alain J. P. R. Sezeur, Cachan, all of France

[73] Assignee: Centre National de la Recherche Scientifique, Paris, France

[21] Appl. No.: 750,414

[22] Filed: Jun. 28, 1985

[51] Int. Cl.[4] .............................................. A61N 5/12
[52] U.S. Cl. ..................................... 128/1.1; 128/1.2; 128/20; 128/344
[58] Field of Search ................... 128/1.1, 1.2, 20, 344; 378/65, 68

[56] References Cited

U.S. PATENT DOCUMENTS 2,959,166  11/1960  Clayton .................................. 128/1.2
4,312,353   1/1982  Shahbabian ............................ 128/20
4,422,447  12/1983  Schiff .................................... 128/344

OTHER PUBLICATIONS

"Cancer of the Stomach" by Pack Livingston, *American Journal of Surgery*, vol. 51, 1941, p. 494.

Primary Examiner—William E. Kamm
Assistant Examiner—Randy Citrin
Attorney, Agent, or Firm—Bell, Seltzer, Park & Gibson

[57] ABSTRACT

The invention relates to a novel method of protecting human and animal organs against radiation. A foldable and unfoldable bladder prosthesis such as disclosed in applicants' U.S. Pat. Nos. 4,311,659 and 4,497,074 is placed in position in the body of the patient who has been operated on for a tumor. The balloon is placed in position in the operational site, after excision or reduction of the tumor and prior to treatment by ionizing radiation. This confers on the balloon the role of a protective device against the radiation of normal tissues and organs which are situated in the path of the radiation. It creats a "neutral" channel free from the presence of tissues or organs which can be injured by the ionizing radiation.

15 Claims, 3 Drawing Figures

METHOD FOR PROTECTING HUMAN OR ANIMAL ORGANS AGAINST RADIATION

BACKGROUND OF THE INVENTION

The present invention relates to a novel method for protecting from radiation, human or animal organs in a patient exposed to such radiation.

Post operative radiation after excision of a tumor is frequently dangerous for the patient in that it causes lesions of normal tissues situated in the path of the radiation, which lesions are manifested by the appearance of evolutive fibroses, alterations and necroses. In particular, post-operative abdominal irradiation after excision of retroperitoneal tumors cannot be contemplated by reason of risk to the digestion, nor post-operative irradiation after excision of certain pelvic tumors, particularly vesical, uterine, ovarian, rectal tumors, etc...

Now, given the certain risk of recurrence of retroperitoneal sarcomas, it is necessary to be able to irradiate the tumoral site; however the risks involved by such radiation require, to permit the use of this therapy, means to be available which enable necroses and other post-radiation lesions of the normal tissues which are situated in the path of the radiation, to be avoided.

Applicants have invented (cf. French Patent Application No. 76 09794 and corresponding U.S. Pat. Nos. 4,311,659 and 4,497,074) a foldable and unfoldable bladder prosthesis which is distinguised by the fact that it is preferaby formed of silicone elastomer and that it has a substantially spherical or perferably ovoid general shape, with respectively two pairs of folds which each extend over one side of the bladder, in which opposite folds are joined by a substantially flat wall and two folds of one pair are joined by two folds, themselves joined by a backfold. The thus constituted bladder prothesis presents, in cross-section, the shape of two $W_s$ lying in opposite directions and joined symmetrically by their outer cheeks, which are the flat walls which join two opposite folds, whilst the inner crests of the W, which are the above-said backfolds, are substantially touching and the four cheeks of each W are substantially in contact in pairs at all points. Through this fact, the residual volume of the bladder prostheses which are the subject of the aforesaid patents, that is to say its internal volume in the empty state or in the absence of internal pressure, is practically nil.

Applicants have been able to demonstrate in the course of their studies of surgical research and partial or total replacement of organs, that the bladder prosthesis that they have previously proposed, surprisingly and unexpectedly has other applications which further increases its value in medicine.

Applicants have in fact established now that the placing in position of a balloon having the characteristics of said bladder prosthesis, in the body of a patient who has undergone operation for a tumor, and more particularly the placing in position at the site of the operation, after excision or reduction of the tumor, and prior to treatment by ionising radiation, confers on this balloon the role of protective device against radiation of the normal tissues and organs which are situated in the path of the radiation.

BRIEF DESCRIPTION OF THE DRAWINGS

The invention will be better understood from the additional description which follows and from the accompanying drawings, in which.

GENERAL DESCRIPTION OF THE INVENTION

In accordance with the present invention, the placing in position of the balloon in the body of the patient, repells or represses, the tissues and organs which are normally to be found in the path of the radiation, thus creating a "neutral" channel, that is to say a space free from the presence of tissues or organs which can be harmed by the ionising radiation, which is traversed by said radiation when the latter is applied to irradiate only the bed of the tumor, excluding the environmental tissues and organs.

Figure 1:
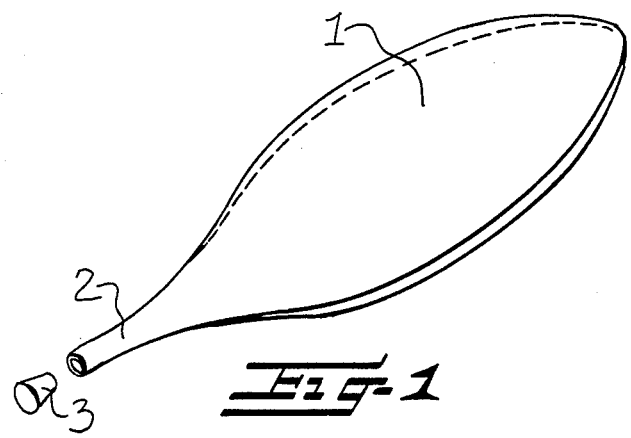
FIG. 1 is a perspective view showing the general shape of a balloon according to the present invention.
Figure 2:
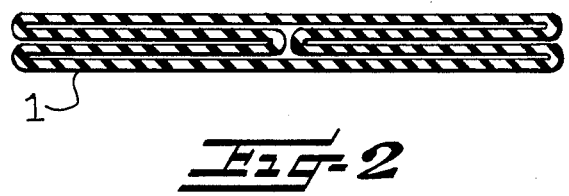
FIG. 2 is a cross-sectional view of a balloon according to the present invention in the empty state.
Figure 3:
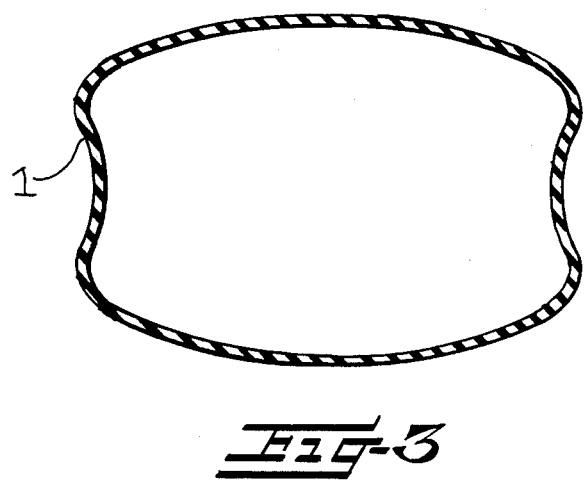
FIG. 3 is a cross-sectional view of the balloon of FIG. 2 in the filled state.

Also in accordance with the present invention, a silicone elastomer balloon (1) having the form and structure which are the subject of French Patent Application No. 76 09794 and U.S. Pat. No. 4,497,074 (as shown in FIGS. 1–3) is placed in position surgically, immediately after the excision or reduction of a tumor, at the end of the operation, in the operational sites, whilst a silicone elastomeric tube 2 provided at one of the ends of its ovoid form, in accordance with the aforementioned patents and which permit its filling and its evacuation, is withdrawn through a counter-incision and fixed firmly to the skin, after which the surgical operational wound is closed and treatment by ionising radiation is undertaken substantially after healing of the surgical operation wound, the extraction of the balloon being effected immediately after the end of the treatment by radiation, or, optionally, removing it, after each radiation session, in case of pain.

In a preferred embodiment of the method of treatment according to the invention, the balloon is inflated after its placing in position and before the closing of the surgical operational wound, by means of a radio-opaque solution, to check radiologically the position of the balloon.

According to a modality of this method of treatment, the radio-opaque solution is removed from the balloon through the aforementioned silicone elastomeric tube 2, at the time of closing the surgical operational wound, after the radiological check of its position has been carried out and said position possibly corrected.

According to another modality of this method of treatment, the balloon remains inflated by the aforementioned radio-opaque solution throughout the duration of the radiation treatment, which pemits permanent radiological checking of its position after the closing of the surgical operational wound and throughout the duration of the radiation treatment.

According to yet another modality of this method of treatment, the distal end, fixed to the skin, of the tube associated with the balloon, is blocked removably by a suitable plug 3.

According to another modality of this method of treatment, the radio-opaque solution is introduced without pressure into the balloon, with the aim or eliminating to the maximum the risks of bursting of the balloon whose walls are rendered fragile by the radiation.

Acording to yet another modality of this method of treatment, the extraction of the balloon from its operational site, at the end of the radiation treatment, to empty it at the end of each radiation session, in case of pain, is carried out when the balloon has been previously deflated, through a very small incision made in a parietal zone close to the operational site.

In accordance with this modality of practising the method of treatment to the invention, the extraction of the balloon is effected by passage through the counter-incision which forms the exit orifice of the tube for admitting and removing liquid for inflating the balloon, previously widened to the desired dimensions.

In any event, the incision that it is necessary to form or to widen to permit the extraction of said balloon, is of small size by reason of the very small volume empty of the balloon.

Post-operational checking by X-ray examination of the abdomen, enables the inflated balloon to be located by filling with the radioopaque solution and confirms the absence of tissues and/or organs in the field of the radiation.

Tomodensitometry carried out for the same purpose, also confirms the absence of tissues and/or organs in the field of radiation.

In accordance with the invention, the radiation treatment is undertaken, after healing of the surgical operational wound, at doses of 45 to 50 gy, (1 gy=100 rods) with an optional local overdose, in case of any need.

Also in accordance with the invention, the duration of the radiation treatment which forms part of the method of treatment according to the present invention, is of the order of 5 to 7 weeks.

In accordance with the invention, the frequency of the radiation sessions is from 2 to 4 weekly, and is preferably 3 sessions per week.

The method of treatment according to the present invention has been illustrated in the following by an example of its application to the protection of the small intestine against ionising radiation, by the placing in position of a silicone elastomeric balloon, in accordance with the features of the patents of applicants which have been mentioned above. It is however well understood that this example, which is given purely by way of illustration of the invention, has no limiting character.

DESCRIPTION OF A PARTICULAR EMBODIMENT

EXAMPLE

Whereas post-operational abdominal radiation after excision of retroperitoneal tumors could not be envisaged with effectiveness by reason of the digestive risk, the surgical placing in position, in accordance with the present invention, in the operational site, of a silicone elastomeric balloon of form substantially spherical or preferably ovoid in the state of repletion and folded on itself in the state of complete evacuation, and of which one of the ends bears a tube also of silicone elastomer which permits the filling and evacuation thereof, permits the digestive tract to be pushed back, thus creating a "neutral" channel from which tissues and organs are absent, through which the tumoral site is irradiated without risk.

The complete peritoneal or extra-peritoneal tolerance has been verified and proved experimentally in the dog.

Surgical placing in position of the balloon is done after excision of the mass or simple tumoral reduction, whether this excision is done transperitoneally or retroperitoneally, by the lumbar, lumbar-iliac, medium or transversal route. It is useful to place at the level of the limits of the tumoral zone, metal clips which can serve as reference points on radiation. Hemostasis must be carefully maintained. At the end of the operation, the balloon is withdrawn from its preserving sheath and rinsed with physiological serum. It is then placed in the operational site. The supply tube of the balloon is taken out through a counter-incision and firmly fixed to the skin. The balloon does not need to be fixed. It is on the other hand inflated before closing the abdominal wall, this in order to check its position well with the belly open. It may be left inflated or on the contrary evacuated at the time of closing. It is preferable to leave it inflated with a radio-opaque solution which permits its position to be checked radiologically after the closing and in the course of the radiation. In all cases the distal end of the evacuator tube is closed by a plug provided for this purpose.

Two suction drains are placed in position around the balloon and are left only 48 hours at the maximum.

Subsequently, the wall will be carefully monitored and any redness will necessitate an anti-staphylococcus treatment whilst awaiting the results of samplings.

Irradiation will only be started after healing of the wall, preferably towards the 20th day.

The doses administered were 45 gy, with an optional local overdose if necessary, preferably three times per week, for about 5 weeks.

The balloon is deflated from the last day of irradition or between sessions in the case of pain.

It is withdrawn after irradiation, in the operating room. The exit orifice of the evacuator tube is widened by 4 to 5 cm under local anesthesia, then the deflated balloon is withdarwn without difficulty. A suction drain is placed in position in the cavity, after bacteriological checking. This drain is left in position for 3 to 4 days.

The treatment which has just been described was applied to three patients of which:

one was afflicted with a voluminous malignant hystiocytofibrosarcoma, the two others had a psoas rabdomyosarcoma, of which one was recurrent.

The immediate results were as follows:

simple sequelae without recurrence for six months for the fibrosarcoma checked with the C.A.T. scan;

simple sequelae without recurrence at one year for the psoas rabdomyosarcoma treated in the initial stage;

lymph flow and pulmonary metastases treated by chemotherapy for the case treated in the course of a recurrance;

absence of radiation intestine (that is to say injured by the ionising radiation) in all patients.

The necessity of irradiating the tumoral site is justified for all retroperitoneal sarcomas, considering the positive risk of recurrence for these tumors, but can also be suggested, for certain localised pelvic tumors whose excision has been incomplete (vesical, uterine, ovarian, rectal, etc. . . . tumors).

Thus, due to the placing in position, in accordance with the present invention, of the foldable and unfoldable balloon described in the foregoing, by repelling tissues and organs, the appearance in the path of the ionising radiation, of lesions of these tissues or organs, such as ulcerations, necroses, developing fibroses, is avoided.

We claim:

1. A method of treatment comprising placing in the body of a patient operated upon for a tumor, at the operating site, after excision or reduction of the tumor in the cavity left by the exeresis of the tumor, and prior to treatment by ionizing radiation, an elastomeric balloon which in an evacuated state is folded upon itself and relatively small in volume, filling the balloon to enlarge it into a substantially spherical form and to push aside adjacent tissues and organs surrounding the tumor site for freeing it from the presence of healthy tissues or organs which can be injured by ionizing radiation, and irradiating the tumor site with ionizing radiation from an external source while the balloon is in place.

2. A method according to claim 1 wherein the balloon has at one of its ends an elastomeric tube having a free end for filling and evacuating of the balloon, and wherein said step of placing the balloon in the body of the patient includes positioning the free end of the tube outside the body of the patient and thereafter closing the surgical operation wound, and wherein said step of irradiating the tumor site is undertaken substantially after healing of the surgical operation wound.

3. A method according to claim 2 including the step, performed after the end of the radiation treatment, of extracting the balloon from the patient through a small cutaneous incision.

4. Method of treatment according to claim 3, wherein the extraction of the balloon from the operational site, at the end of the radiation treatment, is carried out when the balloon has been previously deflated, through a very small incision formed in the parietal zone close to the operational site.

5. Method of treatment according to claim 3, wherein the extraction of the balloon from the operational site, is effected by passage through the counter-incision which forms the exit orifice for the tube for admission and removal of liquid for inflating the balloon, previously widened to the desired dimensions.

6. Method of treatment according to claim 2, wherein the balloon is filled after its placing in position and before the closing of the surgical operational wound, by means of a radio-opaque solution, for radiological checking of the position of the balloon.

7. Method of treatment according to claim 6, wherein the radio-opaque solution is removed from the balloon through the aforementioned elastomeric tube, at the time of closing the surgical operational wound, and after the radiological check of its position has been carried out and said position corrected if necessary, and wherein the balloon is thereafter filled prior to said irradiating step.

8. Method of treatment according to claim 6, wherein the balloon remains filled by the aforementioned radio-opaque solution throughout the duration of the radiation treatment, which permits a permanent radiological checking of its position after the closing of the surgical operational wound and throughout the duration of the radiation treatment.

9. Method of treatment according to claim 6, wherein the radio-opaque solution is introduced into the balloon without application of external pressure on the solution, for the purpose of eliminating to the maximum the risks of bursting of the balloon whose walls are rendered fragile by the radiation.

10. Method of treatment according to claim 2, wherein the free end of the tube associated with the balloon is removably closed by a suitable plug.

11. A method of treatment comprising placing in the body of a patient operated upon for a tumor at the operating site, after excision or reduction of the tumor, in the cavity left by the exeresis of the tumor, and prior to the treatment by ionizing radiation an elastomeric balloon which, in the evacuated state, has two pairs of folds, each extending over one side of the balloon, in which two opposite folds are joined by a substantially flat wall and two folds of one pair are joined by two folds, themselves joined by a counterfold, said balloon having, in section, the form of two Ws lying in opposite directions and joined symmetrically by their outer cheeks, while their inner crests, constituted by the aforesaid counterfolds are substantially touching and the four cheeks of each W are substantially in contact in pairs at all points, filling the balloon to enlarge it into a substantially spherical form and to push aside adjacent tissues and organs surrounding the tumor site for freeing it from the presence of healthy tissues or organs which can be injured by ionizing radiation, the wall of said balloon fitting closely with the peritoneal wall, and irradiating the tumor site thus freed from healthy tissues or organs, with ionizing radiation from an external source while the balloon is in place.

12. Method of treatment according to claim 1, wherein the radiation treatment is undertaken, after healing of the surgical operational wound, at doses of 45 to 50 gy, with a possible local overdose, in case of need.

13. Method of treatment according to claim 12, wherein the duration of the radiation treatment is of the order of 5 to 7 weeks.

14. Method of treatment according to claim 13, wherein the radiation treatment is carried out at the rate of 2 to 4 sessions per week.

15. Method of treatment according to claim 14, wherein the radiation treatment is carried out at the rate of 3 sessions per week.

* * * * *